(12) United States Patent
Tenne

(10) Patent No.: US 8,118,859 B2
(45) Date of Patent: Feb. 21, 2012

(54) OCCLUSION DEVICE COMBINATION OF STENT AND MESH HAVING OFFSET PARALLELOGRAM POROSITY

(75) Inventor: Dirk Tenne, Miami Beach, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 984 days.

(21) Appl. No.: 11/420,523

(22) Filed: May 26, 2006

(65) Prior Publication Data

US 2007/0276470 A1    Nov. 29, 2007

(51) Int. Cl.
*A61F 2/06* (2006.01)
(52) U.S. Cl. ..................................... 623/1.23
(58) Field of Classification Search ............... 623/1.23, 623/1.17, 1.39, 1.4, 1.44, 1.15, 1.11; 606/200, 606/191, 199, 108
See application file for complete search history.

(56) References Cited

U.S. PATENT DOCUMENTS

| | | | |
|---|---|---|---|
| 4,390,599 A | 6/1983 | Broyles | |
| 4,475,972 A * | 10/1984 | Wong | 156/167 |
| 4,864,824 A | 9/1989 | Gabriel et al. | |
| 4,981,756 A | 1/1991 | Rhandhawa | |
| 5,061,914 A | 10/1991 | Busch et al. | |
| 5,082,359 A | 1/1992 | Kirkpatrick | |
| 5,178,957 A | 1/1993 | Kolpe et al. | |
| 5,197,978 A | 3/1993 | Hess | |
| 5,288,230 A | 2/1994 | Nikutowski et al. | |
| 5,288,711 A | 2/1994 | Mitchell et al. | |
| 5,334,216 A | 8/1994 | Vidal et al. | |
| 5,360,397 A | 11/1994 | Pinchuk | |
| 5,397,355 A * | 3/1995 | Marin et al. | 623/1.2 |
| 5,403,700 A | 4/1995 | Heller et al. | |
| 5,516,781 A | 5/1996 | Morris et al. | |
| 5,543,019 A | 8/1996 | Lee et al. | |
| 5,563,146 A | 10/1996 | Morris et al. | |
| 5,607,463 A | 3/1997 | Schwartz et al. | |
| 5,629,077 A | 5/1997 | Turnlund et al. | |
| 5,646,160 A | 7/1997 | Morris et al. | |
| 5,656,036 A | 8/1997 | Palmaz | |
| 5,669,977 A | 9/1997 | Shufflebotham et al. | |
| 5,681,575 A | 10/1997 | Burrell et al. | |
| 5,685,961 A | 11/1997 | Pourrezaei et al. | |

(Continued)

FOREIGN PATENT DOCUMENTS

EP    0759730    5/1997

(Continued)

OTHER PUBLICATIONS

Neurological Research, Lieber et al., The physics of endoluminal stenting in the treatment of cerebrovasilar aneurusms, 2002.

(Continued)

*Primary Examiner* — Corrine M McDermott
*Assistant Examiner* — Christina Lauer
(74) *Attorney, Agent, or Firm* — Cook Alex Ltd.

(57) ABSTRACT

An occlusion device for implantation within a body vessel is provided with a screen member and an associated support member. The occlusion device is radially expandable from a compressed condition, suitable for inserting the device in an introducer, to a deployed or expanded condition within a vessel. The screen member includes a plurality of substantially parallelogram-shaped openings in the compressed condition arranged in longitudinal rows, the openings being axially offset from each other. The porosity of the screen member is less than the porosity of the support member in the expanded condition.

17 Claims, 3 Drawing Sheets

U.S. PATENT DOCUMENTS

| | | | |
|---|---|---|---|
| 5,735,892 A | | 4/1998 | Myers et al. |
| 5,744,958 A | | 4/1998 | Werne |
| 5,753,251 A | | 5/1998 | Burrell et al. |
| 5,766,176 A | * | 6/1998 | Duncan .................. 606/281 |
| 5,766,710 A | | 6/1998 | Turnlund et al. |
| 5,770,255 A | | 6/1998 | Burrell et al. |
| 5,810,870 A | | 9/1998 | Myers et al. |
| 5,824,043 A | * | 10/1998 | Cottone, Jr. .................. 623/1.13 |
| 5,824,054 A | | 10/1998 | Khosravi et al. |
| 5,843,289 A | | 12/1998 | Lee et al. |
| 5,902,317 A | | 5/1999 | Kleshinski et al. |
| 5,908,409 A | | 6/1999 | Rinehart et al. |
| 5,925,038 A | | 7/1999 | Panescu et al. |
| 5,925,075 A | | 7/1999 | Myers et al. |
| 5,938,697 A | | 8/1999 | Killion et al. |
| 5,945,153 A | | 8/1999 | Dearnaley |
| 5,951,586 A | | 9/1999 | Berg et al. |
| 6,015,402 A | | 1/2000 | Sahota |
| 6,017,553 A | | 1/2000 | Burrell et al. |
| 6,027,526 A | | 2/2000 | Limon et al. |
| 6,043,451 A | | 3/2000 | Julien et al. |
| 6,096,175 A | | 8/2000 | Roth |
| 6,174,329 B1 | | 1/2001 | Callol et al. |
| 6,203,732 B1 | | 3/2001 | Clubb et al. |
| 6,238,686 B1 | | 5/2001 | Burrell et al. |
| 6,270,872 B1 | | 8/2001 | Cline et al. |
| 6,296,661 B1 | * | 10/2001 | Davila et al. .................. 623/1.13 |
| 6,312,463 B1 | | 11/2001 | Rourke et al. |
| 6,319,277 B1 | | 11/2001 | Rudnick et al. |
| 6,322,588 B1 | | 11/2001 | Ogle et al. |
| 6,325,824 B2 | | 12/2001 | Limon |
| 6,342,067 B1 | | 1/2002 | Mathis et al. |
| 6,402,771 B1 | * | 6/2002 | Palmer et al. .................. 606/200 |
| 6,432,116 B1 | | 8/2002 | Callister et al. |
| 6,436,132 B1 | | 8/2002 | Patel et al. |
| 6,447,478 B1 | | 9/2002 | Maynard |
| 6,471,721 B1 | | 10/2002 | Dang |
| 6,527,919 B1 | | 3/2003 | Roth |
| 6,533,905 B2 | | 3/2003 | Johnson et al. |
| 6,537,310 B1 | | 3/2003 | Palmaz et al. |
| 6,605,111 B2 | | 8/2003 | Bose et al. |
| 6,627,246 B2 | | 9/2003 | Mehta et al. |
| 6,645,243 B2 | | 11/2003 | Vallana et al. |
| 6,660,032 B2 | | 12/2003 | Klumb et al. |
| 6,666,882 B1 | | 12/2003 | Bose et al. |
| 6,673,106 B2 | | 1/2004 | Mitelberg et al. |
| 6,726,993 B2 | | 4/2004 | Teer et al. |
| 6,786,920 B2 | | 9/2004 | Shannon et al. |
| 6,805,898 B1 | | 10/2004 | Wu et al. |
| 6,818,013 B2 | | 11/2004 | Mitelberg et al. |
| 6,865,810 B2 | | 3/2005 | Stinson |
| 6,921,414 B2 | * | 7/2005 | Klumb et al. .................. 623/1.15 |
| 6,938,668 B2 | | 9/2005 | Whicher et al. |
| 6,955,685 B2 | | 10/2005 | Escamilla et al. |
| 2001/0039449 A1 | | 11/2001 | Johnson et al. |
| 2004/0098094 A1 | | 5/2004 | Boyle et al. |
| 2005/0010175 A1 | | 1/2005 | Beedon et al. |
| 2005/0154449 A1 | | 7/2005 | Elmaleh |
| 2008/0004653 A1 | * | 1/2008 | Sherman et al. .............. 606/195 |

FOREIGN PATENT DOCUMENTS

| | | |
|---|---|---|
| EP | 0847733 A1 | 12/1997 |
| EP | 0641224 B1 | 8/1998 |
| EP | 1099004 A1 | 7/1999 |
| EP | 0824900 B1 | 4/2003 |
| EP | 01099004 B1 | 9/2004 |
| GB | 2331998 A | 6/1999 |
| WO | 9307924/WO A1 | 4/1993 |
| WO | 9323092/WO A1 | 11/1993 |
| WO | 9425637/WO A1 | 11/1994 |
| WO | 95137041/WO A1 | 5/1995 |
| WO | 9726026/WO A2 | 7/1997 |
| WO | 9966966/WO A1 | 12/1999 |
| WO | 0004204/WO A1 | 1/2000 |

OTHER PUBLICATIONS

American Journal of Neuroradiology, Higashida et al., Initial clinical experience with a new self-expanding nitinol stent for the treatment of intracranial cerebral aneurysms: the Cordis Enterprise stent, Aug. 2005.

Spine; Hellier, Hedman, Kostuik; Wear Studies for development of an intervertebral disc prosteses; Jun. 1992; US.

Biomaterials; LI; Behaviour of titanium and titania-based ceramics in vitro and in vivo; Feb. 2003; US.

Elsevier; Banks et al,; Ion bombardment modification of surfaces in biomedical applications; 399-434; 1984; Netherlands.

Advances in Bioengineering; Chung, Chang, Han; Development of thin metal film deposition process for the intravascular catheter; Conference; Nov. 14, 1999; US.

Journal of Materials Processing Technology; Kola, Daniels, Cameron, Hashmi; Magnetron suputtering of TiN protective coatings for medical applications; 422-430; Jan. 1996; Ireland.

Journal of Biomedical Materials Research; Yuhta et al ; Blood compatibility of sputter deposited alumina films; 271-224; Feb. 1994.

Society for Biomaterials; Ong, Lucas, Lacefield, Rigney; Properties of calcium-phosphate coatings produced by ion-beam sputter deposition; Conference; May 1, 1991; US.

Asaio; Zabetakis, Cotell, Chrisey, Auyeung; Pulsed laser deposition of thin film hydroxyapatite. Applications for flexible catheters; 896-899; Jul. 1994; US.

* cited by examiner

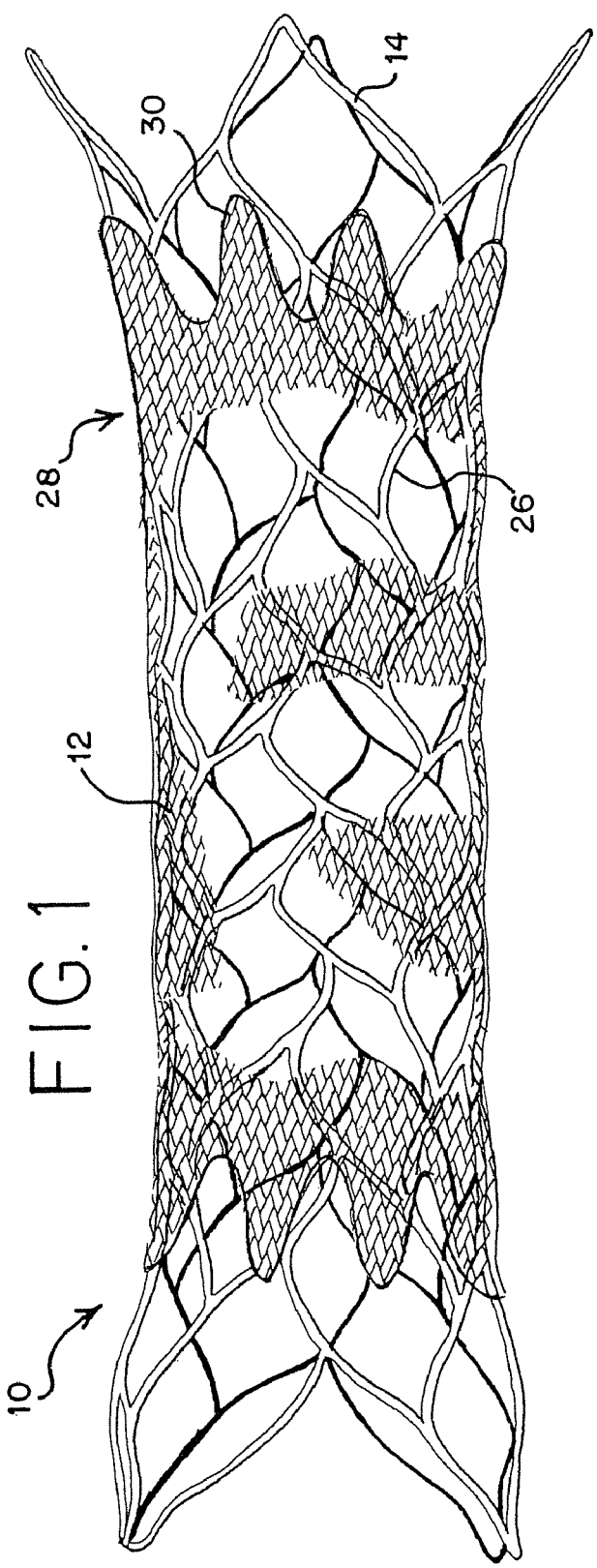
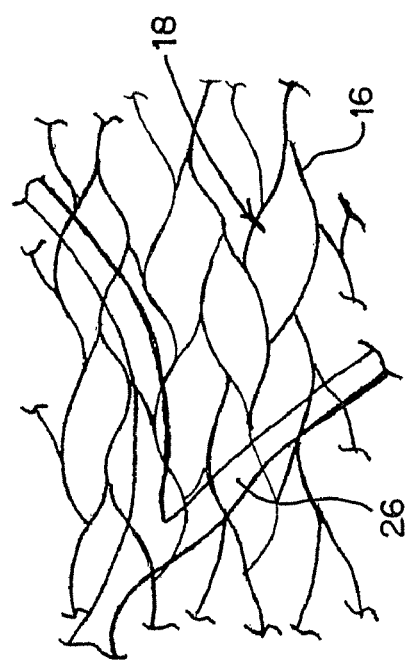

OCCLUSION DEVICE COMBINATION OF STENT AND MESH HAVING OFFSET PARALLELOGRAM POROSITY

FIELD OF THE INVENTION

This invention generally relates to medical devices that are implantable within a human subject and that have occlusion capabilities for treating defective or diseased body vessels. More particularly, this invention relates to an occlusion device including a support member and a screen member.

DESCRIPTION OF RELATED ART

Medical devices that can benefit from the present invention include those that are characterized by hollow interiors and that are introduced endoluminally and expand when deployed so as to protect or plug up a location of concern within the patient. These are devices that move or are moved between collapsed and expanded conditions or configurations for ease of deployment through catheters and introducers. The present disclosure focuses upon occlusion devices for diseased locations within vessels of the body, especially devices sized and configured for implantation within the vasculature, as well as devices for neurovascular use.

Endoluminal stents typically have a relatively open structure, with pores or openings in the surface that can allow for endothelialization and more permanent fixture of the stent within the vessel after implantation. Certain stents have an especially open structure in order to allow blood flow through the openings and to peripheral arteries after implantation of the stent adjacent to an aneurysm. Typically, the pores or openings are added by masking and/or etching techniques or laser or water jet cutting.

When thin film meshes are combined with a stent, the mesh typically is provided with a porosity less than that of a stent when expanded or deployed within a body vessel. Thus, they are useful for applications requiring a lower porosity. However, meshes are generally not rugged enough for a wide range of applications, such as supporting a stenosed vessel, and they typically can be provided with a skeletal support structure, oftentimes a stent. Examples of implantable grafts used in combination with an underlying support structure can be seen in Boyle, Marton and Banas U.S. Patent Application Publication No. 2004/0098094, which is hereby incorporated by reference hereinto. This publication proposes implantable endoluminal grafts having a pattern of slit openings that move from a closed condition to an open condition that could be characterized as having a generally diamond-shaped condition. Underlying structural support elements support the microporous metallic thin film graft. One potential drawback of the grafts is that the transition from the closed slit shape to the open diamond shape can be overly stressful on the film, especially at the ends of the slit, thereby leading to film rupture during deployment.

Accordingly, a general aspect or object of the present invention is to provide an occlusion device less susceptible to film rupture during deployment.

Another aspect or object of this invention is to provide an occlusion device having a screen member that more closely follows a support member of the device during expansion for deployment than do other mesh members.

Other aspects, objects and advantages of the present invention, including the various features used in various combinations, will be understood from the following description according to preferred embodiments of the present invention, taken in conjunction with the drawings in which certain specific features are shown.

SUMMARY OF THE INVENTION

In accordance with an aspect of the present invention, an occlusion device includes a generally tubular support member radially expandable from a compressed condition to an expanded condition for occlusion action within a body vessel. The occlusion device also includes a generally tubular screen member associated with at least a portion of the support member and radially expandable from a compressed condition to an expanded condition with the support member. The screen member further includes a plurality of offset substantially parallelogram-shaped openings in the compressed condition. These openings are defined by a pair of upwardly inclined parallel edges intersecting a pair of downwardly inclined parallel edges. One pair of parallel edges is longer than the other pair of parallel edges. In an illustrated arrangement, most of these openings are circumferentially adjacent a plurality of other such openings. The support member and screen member each have a porosity in the expanded condition, with the porosity of the screen member being less than that of the support member.

In accordance with another aspect of the present invention, an occlusion device includes a generally tubular inner support member radially expandable from a compressed condition to an expanded condition for occlusion action within a body vessel. A generally tubular outer support member and a generally tubular screen member are also radially expandable with the inner support member. The screen member is received between at least a portion of the inner support member and at least a portion of the outer support member. The screen member further includes a plurality of offset substantially parallelogram-shaped openings in the compressed condition. The openings are defined by a pair of upwardly inclined parallel edges intersecting a pair of downwardly inclined parallel edges. One pair of parallel edges is longer than the other pair of parallel edges. In an illustrated arrangement, most of these openings are circumferentially adjacent a plurality of other such openings. The support members and screen member each have a porosity in the expanded condition, with the porosity of the screen member being less than that of the support members.

In accordance with yet another aspect of the present invention, an occlusion device includes a generally tubular support member radially expandable from a compressed condition to an expanded condition for occlusion action within a body vessel. A generally tubular inner screen member, which is at least partially received within the support member, and a generally tubular outer screen member, which overlays at least a portion of the support member, are also radially expandable with the support member. The screen members each include a plurality of offset substantially parallelogram-shaped openings in the compressed condition. The openings are defined by a pair of upwardly inclined parallel edges intersecting a pair of downwardly inclined parallel edges. One pair of parallel edges is longer than the other pair of parallel edges. In an illustrated arrangement, most of these openings are circumferentially adjacent a plurality of other such openings. The support member and screen members each have a porosity in the expanded condition, with the porosities of the screen members being less than that of the support member.

BRIEF DESCRIPTION OF THE DRAWINGS

FIG. 1 is a side elevational view of an occlusion device according to an aspect of the present invention, with some parts broken away for clarity;

FIG. 2 is a detail view of a portion of the occlusion device of FIG. 1;

DESCRIPTION OF THE PREFERRED EMBODIMENTS

Figure 3:
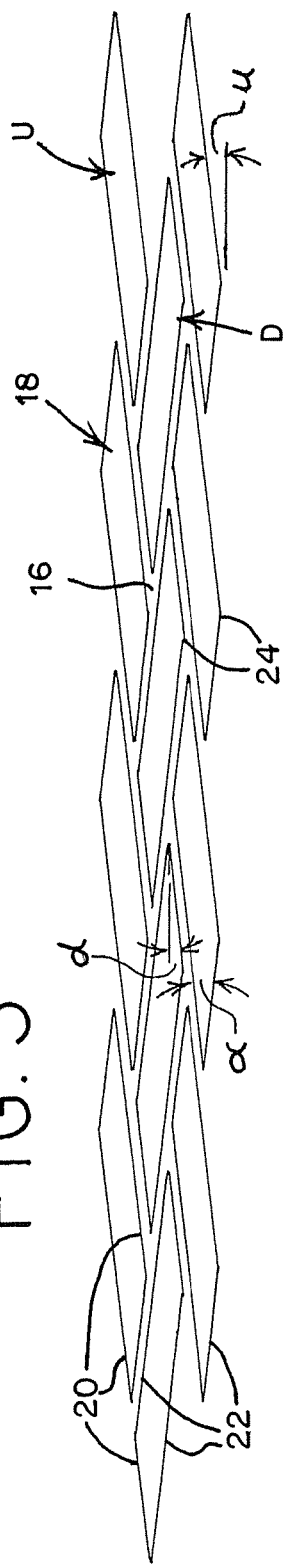
FIG. 3 is an enlarged plan view of a parallelogram cell pattern suitable for application to a screen member.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The occlusion device 10 of FIG. 1 is a generally tubular structure with a generally tubular screen member 12 and a generally tubular support member 14. The screen member 12 is illustrated in FIG. 1 with selected portions broken away to show an underlying portion of the support member 14. The occlusion device 10 and its constituent parts are radially expandable from a compressed condition, for delivery in an introducer, to an expanded condition within a body vessel to support the same. An occlusion device according to the present invention may be deployed with known devices and according to known methods.

In the illustrated embodiment of FIG. 1 and FIG. 2, the screen member 12 overlays at least a portion of the support member 14. Preferably, the screen member 12 is provided as a mesh which is comprised of a plurality of cells 16 defining substantially parallelogram-shaped openings 18. These cells 16 are referred to herein as "parallelogram cells" and can be seen in greater detail in FIG. 3 as unexpanded and in FIG. 2 as expanded. As will be appreciated from the description herein, the risk of film rupture is substantially decreased because the openings 18 are initially formed with an offset parallelogram shape, so as to address problems associated with other structures, including those that transition from substantially linear closed slits to open diamond-like pores during deployment. The present offset parallelogram openings, in the as-manufactured condition, avoid or minimize stresses and fissures that tend to develop during expansion of other designs.

According to one method of manufacturing the screen member 12, a substantially cylindrical mandrel (not illustrated) is provided. In one embodiment, the mandrel has a diameter of 2.12 mm and is formed of copper. A thin film is formed on the mandrel according to known methods, such as sputtering, and parallelogram-shaped openings are formed in the film, preferably by laser cutting. Forming the openings as parallelograms on a mandrel reduces the material ratio, increases the capability of loading the occlusion device into an introducer, and reduces the risk of film rupture during radial expansion of the occlusion device 10.

FIG. 3 illustrates a pattern that may be repeated along the thin film to create the illustrated offset parallelogram cells 16. As illustrated in FIG. 3, the parallelogram-shaped openings 18 are defined by a pair of upwardly inclined (as viewed in FIG. 3) parallel edges 20 intersecting a pair of downwardly inclined (as viewed in FIG. 3) parallel edges 22, one of which pairs of edges is longer than the other. It will be appreciated that the pattern of FIG. 3 is a two-dimensional representation of a portion of a cylindrical surface along a longitudinal axis; therefore, "upwardly inclined" and "downwardly inclined" designate a general relationship with respect to the longitudinal axis that has a three-dimensional element that is not explicitly illustrated in FIG. 3.

The edges 20, 22 are at an inclination angle "u" or "d", as viewed in FIG. 3, each being less than an opening angle "α" between one of the edges 20 and one of the other edges 22. For example, the inclination angle "u" and/or "d" can be approximately one-half of the opening angle "α".

In a preferred embodiment, the longer edges are at least 1.5 times as long as the shorter edges and can be at least twice as long as the shorter edges. If the upwardly inclined edges 20 are longer than the downwardly inclined edges 22, as indicated generally at "U", the opening has an upward attitude generally represented by inclination angle "u" as viewed in FIG. 3. Otherwise, if the downwardly inclined edges 22 are longer than the upwardly inclined edges 20, as indicated generally at "D", the opening has a downward attitude generally represented by inclination angle "d" as viewed in FIG. 3. Inclination angles "u" and "d" typically are on the order of about 1 degree to about 20 degrees, or to about 15 degrees, typically not greater than about 12 degrees, and often not greater than about 10 degrees.

Preferably, the lowermost point of each opening 18 (as viewed in FIG. 3) is defined by a vertex or corner 24, rather than by an edge 20, 22, such that each opening 18 moves to the generally parallelogrammatic or skewed diamond configuration of FIG. 2 when the screen member 12 is radially expanded. Although illustrated in FIG. 3 with sharp vertices 24, each opening 18 may instead be provided with flattened or blunted corners. At smaller opening sizes, it can become difficult to accurately manufacture tight, angular corners and, even if possible, it may be preferred to flatten or round the corners in order to provide more material between adjacent openings, and thereby further discourage film rupture. Hence, when used herein to describe the shape of the openings as-manufactured or in a compressed condition, the term "parallelogram" includes parallelograms with one or more flattened or blunted or rounded corners and/or parallelograms with edges having some minor degree of curvature.

Preferably, the openings 18 are provided in longitudinal rows according to the pattern of FIG. 3. In the illustrated arrangement, the openings of adjacent rows are axially offset from each other such that the openings from adjacent rows are not in circumferential alignment with each other. For example, each longer edge of the opening is shown adjacent to part of at least two other openings. Typically, it is desirable for the openings 18 in adjacent rows to have opposite attitudes, as shown.

As described above, the screen member 12 is radially expandable and, during deployment, the opening angle "α" will increase as the openings 18 become taller and thinner, as shown in FIG. 2. The axial deformation of the openings with upward attitudes "U" is generally in the opposite direction of that of the openings with downward attitudes "D", so the alternating pattern of FIG. 3 provides circumferential arrays of offset openings that promote axial foreshortening of the screen member 12 that corresponds generally to that of the support member 14. The screen member may be provided with identical parallelogram cells (the upward attitude cells being mirror images of the downward attitude cells in the illustrated embodiment) arranged in a uniform pattern, which results in substantially uniform radial expansion properties at all points of the screen member. In the embodiment shown in FIG. 3, the offset parallelogram openings are arranged in axially aligned rows. Alternating rows are staggered with respect to each other so that a given parallelogram opening is adjacent to two parallelograms in an adjacent row when viewed in a circumferential direction. Alternatively, the parallelogram-shaped openings may be provided in a non-uniform array, or differently sized parallelogram openings may be formed along the surface of the thin film.

The parallelogram openings 18 of FIG. 3 are illustrated with identical as-manufactured opening angles "α", typically between approximately 5 and 30 degrees, and can be between 5 and approximately 15 degrees. In differing embodiments, the angle can be about 7 degrees, about 8 degrees, about 9 degrees, and about 13 degrees. It will be appreciated that a range of opening sizes are possible for a given opening angle "α", depending on the length of the edges. In general, the size of the openings is directly related to the porosity of the screen member, such that larger openings will result in greater porosity. Porosity can be varied without changing the opening angle. The number of openings about a circumference of the screen member depends on several factors, including the size of the openings, the diameter of the screen member, and the spacing between the openings. It will be appreciated that any number of openings may be provided without departing from the scope of the present invention.

Preferably, the openings are sufficiently spaced to result in an opening-to-material ratio falling within the range of approximately 1.5:1 (or approximately 60% open space and 40% film material) and 4:1 (or approximately 80% open space and 20% film material). In one embodiment, a thin film is applied to a mandrel diameter of 2.12 mm, and then an alternating two-row pattern is repeated 75 times around a circumference of the film, with an opening angle of 7.57 degrees and a spacing between adjacent openings of 0.007 mm, also referred to as the strut width. Typical strut widths can be between about 0.005 mm and about 0.01 mm.

The screen member 12 is radially expandable from a compressed or delivery condition to an expanded or deployed condition, so it is preferably formed of a deformable or semi-rigid material, may have shape memory attributes or not, and may be polymeric or metallic. Suitable polymeric materials include polyolefins such as polypropylenes, polyesters such as polyethylene terephathalate, polyamides, nylons and so forth. Typical screen members will have a thickness of between about 0.05 and about 0.1 mm, such as between about 0.07 and 0.08 mm.

If provided as a metal, the screen member 12 may be substantially comprised of, for example, stainless steel or an alloy such as nickel and titanium alloys or nitinols. Nitinol type metals typically will exhibit superelastic properties. Shape memory materials such as nitinols in an austenite state can be used.

More particularly, when the material is a nitinol, the nitinol may be either a martensite or austenite thin film at human body temperature, which will result in different performance characteristics. If the nitinol is a martensite thin film at body temperature, then it will easily be compressed and inserted into a delivery catheter, then allow radial expansion of the occlusion device without resistance. A martensitic or superelastic nitinol is more likely to easily "go along for the ride" with the support member 14, especially when it expands. If a shape memory material such as a nitinol is an austenite thin film at body temperature, then the screen member will actively return to its as-formed shape if the occlusion device is being designed to facilitate its recapture after being deployed in a body vessel.

The support member 14 preferably is provided as a radially expandable, generally tubular stent, as illustrated in FIG. 1. The support member 14 may take on many different patterns or configurations, such as a self-expanding stent, including those disclosed in U.S. Pat. Nos. 6,673,106 and 6,818,013, both to Mitelberg et al. and both of which are hereby incorporated herein by reference. Alternatively, the support member may be provided as a balloon-expandable stent.

The illustrated support member 14 of FIG. 1 is a self-expanding stent, preferably laser cut from a tubular piece of nitinol to form a skeletal structure. The nitinol is preferably treated so as to exhibit superelastic properties at body temperature. The skeletal structure has a thin wall, a small diameter, and when cut forms a plurality of cells which are created by a plurality of interconnected struts 26. Preferably, the cells of the support member 14 are generally approximated by the parallelogram cells 16 of the screen member 12. This allows the screen member 12 and the support member 14 to exhibit similar deformation properties during deployment to a body vessel. Such deformation properties include the extent of foreshortening upon expansion, because differing degrees of foreshortening between the screen member and the support member may lead to undesirable rupture and/or folding of the screen member.

According to one aspect of the present invention, illustrated in FIGS. 1 and 2, the occlusion device is comprised of a screen member 12 overlaying at least a portion of a support member 14. The screen member 12 may be fully or partially affixed to the support member 14 in order to prevent the two from rotating or otherwise moving with respect to each other. Suitable joinder means will depend on the nature of the screen member 12 and on the support member 14, the selection of which means is a routine task for one of ordinary skill in the art. This means may include, but is not limited to, welding, soldering, adhering, crimping, or combinations thereof.

In use, the occlusion device 10 is radially compressed into a delivery condition and inserted into the distal end of an introducer (not shown). The occlusion device 10 may be mounted about a guidewire or a balloon catheter before being compressed and inserted into the introducer. When the occlusion device 10 is compressed, the openings 18 of the screen member 12 move from the relatively open parallelogram shape of FIGS. 1 and 2 to a more closed parallelogram shape having a smaller opening angle "α" in the compressed condition.

Figure 4:
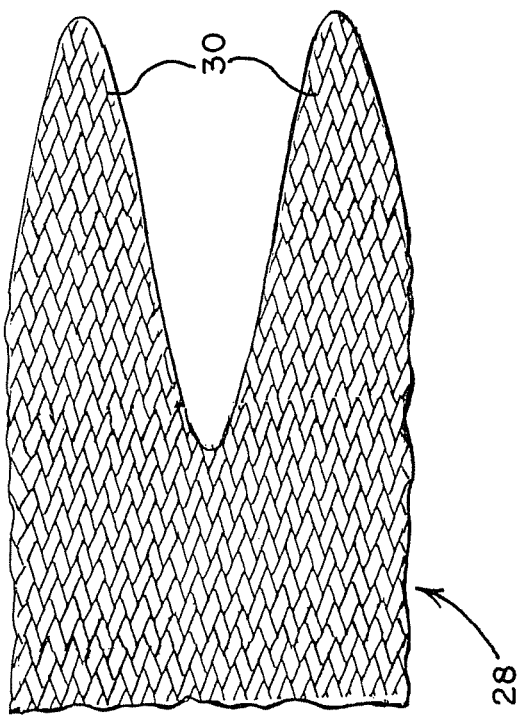
FIG. 4 is a detail view of a screen member edge with a generally sinusoidal configuration.

In order to simplify insertion of the occlusion device 10 into the introducer, the peripheral edges at the axial ends of the screen can be non-linear, in that they do not lie fully within a radial plane. They do not follow a circular path, but instead follow an undulating path to provide "wavy ends." For example, the proximal edge 28 of the screen member 12 may be provided with a generally sinusoidal configuration, as illustrated in greater detail in FIG. 4. A flat or non-undulating edge may become folded upon itself when compressed and inserted into an introducer, thereby increasing friction and the associated push forces. This is analogous to folding that occurs when a mitten is forced into a tight pocket. In the embodiment of FIGS. 1 and 4, extensions 30 of the edge 28 may move toward each other without overlapping when the device is compressed, analogous to gloved fingers moving together when inserted into a tight pocket.

When the occlusion device 10 has been properly loaded, the introducer is moved into the interior of a body vessel and positioned adjacent to a region of the vessel which is to be occluded. Finally, the occlusion device 10 is ejected from the introducer and into the target region. If the support member is not self-expanding, then a balloon is expanded to force the occlusion device 10 against the wall of the vessel.

The screen member 12 and the support member 14 each have a separate porosity in the deployed or expanded condition of FIG. 1. As illustrated, the porosity of the screen member 12 is less than that of the support member 14, which effectively gives the occlusion device 10 an overall porosity less than that of the support member 14 alone.

Figure 5:
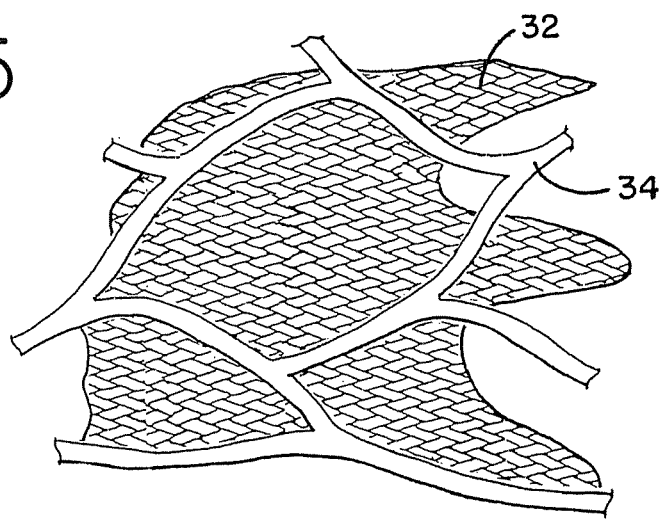
FIG. 5 is a detail view of an occlusion device according to another aspect of the present invention.

The occlusion device may be provided according to a number of various configurations in order to achieve results similar to those described above with regard to the embodiment of FIG. 1. For example, according to one aspect of the present invention, a generally tubular screen member 32 instead may be mounted within a generally tubular support member 34, as illustrated in FIG. 5. With this approach, the support member is external of the screen member.

Figure 6:
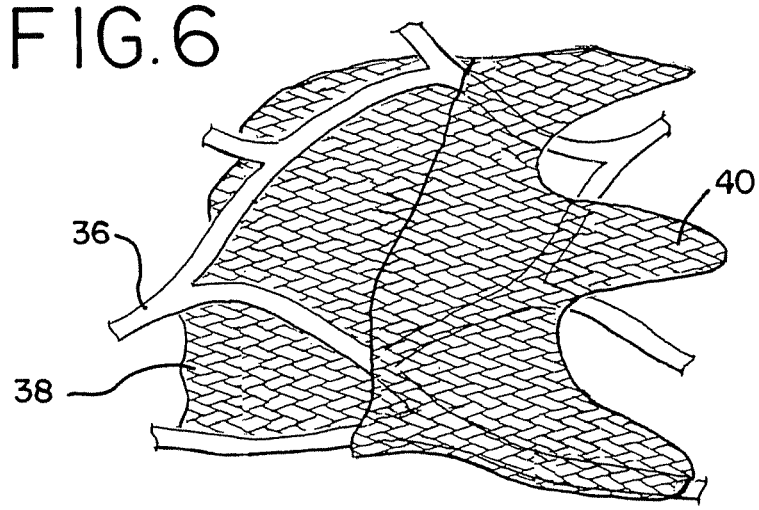
FIG. 6 is a detail view of an occlusion device according to yet another aspect of the present invention, with some parts broken away for clarity.

According to yet another aspect, illustrated in FIG. 6, an occlusion device may be provided with a generally tubular support member 36, a generally tubular inner screen member 38 at least partially received within the support member 36, and a generally tubular outer screen member 40 overlaying at least a portion of the support member 36. Each screen member can be secured to the support member. Also, rather than individually attaching each screen member 38 and 40 to the support member 36, the screen members 38 and 40 may be directly attached to each other, thereby trapping the support member 36.

Figure 7:
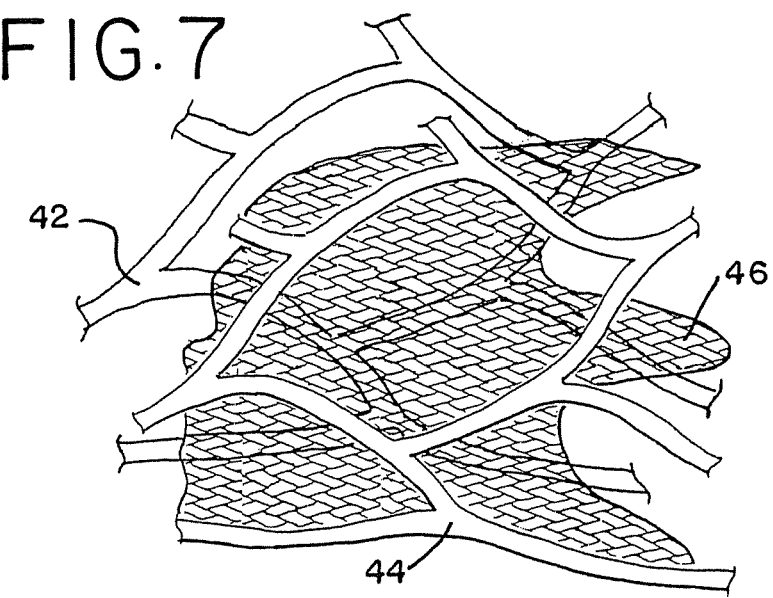
FIG. 7 is a detail view of an occlusion device according to still another aspect of the present invention.

According to still another aspect, illustrated in FIG. 7, an occlusion device may be provided with a generally tubular inner support member 42, a generally tubular outer support member 44, and a generally tubular screen member 46 received between at least a portion of the inner support member 42 and at least a portion of the outer support member 44. Each support member can be secured to the sandwiched screen member. Also, rather than individually attaching each support member 42 and 44 to the screen member 46, the support members 42 and 44 may be directly attached to each other, thereby trapping the screen member 46.

It is to be understood that the various screen members and support members of FIGS. 5-7 conform to the above description of the components of the occlusion device 10 of FIG. 1. Hence, each screen member is radially expandable with the associated support member, has a plurality of substantially parallelogram-shaped openings in both the compressed and expanded conditions, and has a porosity that is less than that of the associated support member in the expanded condition within a body vessel.

The screen member and/or the support member may be coated with an agent, such as heparin or rapamycin, to prevent stenosis or restenosis of the vessel. Examples of such coatings are disclosed in U.S. Pat. Nos. 5,288,711 to Mitchell et al.; 5,516,781 to Morris et al.; 5,563,146 to Morris et al.; and 5,646,160 to Morris et al., all of which are hereby incorporated herein by reference. Other coatings may also be applied without departing from the scope of the present invention.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An occlusion device for occluding at least a portion of a body vessel in a human subject, comprising:
   a generally tubular support member radially expandable from a compressed condition to an expanded condition for occlusion action within a body vessel, wherein the support member has a porosity in at least the expanded condition;
   a generally tubular screen member associated with at least a portion of the support member and radially and circumferentially expandable from a radially and circumferentially compressed condition to a radially and circumferentially expanded condition with the support member, further comprising a plurality of parallelogram-shaped openings in the compressed condition, and wherein the screen member is a thin-film mesh from which the parallelogram-shaped openings had been cut to be circumferentially adjacent to each other and are in a common cylindrical plane, and the screen member has a porosity in the expanded condition less than the porosity of the support member in the expanded condition;
   each said opening is defined by a pair of upwardly inclined parallel edges directly intersecting a pair of downwardly inclined parallel edges wherein upwardly inclined and downwardly inclined designate a general relationship with respect to the longitudinal axis of the screen member, and, wherein one of the pairs of parallel edges is at least about 1.5 times longer than the other one of the pairs of parallel edges, and adjacent directly intersecting edges define an as-manufactured opening angle that is between about 5 and about 30 degrees; and
   respective lowermost ends of adjacent upwardly inclined and downwardly inclined parallel edges of the opening directly engage each other to directly define a vertex that joins said opening with an adjacent opening offset therefrom in that the vertex is at a location spaced away from and between the ends of a said longer edge of the adjacent opening, whereby openings of adjacent rows of openings are axially offset from each other within the common cylindrical plane such that the openings from adjacent rows are not in circumferential alignment with each other.

2. The occlusion device of claim 1, wherein the screen member overlays at least a portion of the support member.

3. The occlusion device of claim 2, further including an additional screen member having a plurality of parallelogram-shaped openings, and wherein the support member overlays said additional screen member.

4. The occlusion device of claim 1, wherein at least a portion of the screen member is received within the support member.

5. The occlusion device of claim 4, further including an additional support member, and wherein the screen member overlays at least a portion of said additional support member.

6. The occlusion device of claim 1, wherein an edge of the screen member has a generally sinusoidal configuration.

7. The occlusion device of claim 1, wherein said screen member has an opening-to-material ratio falling within the range of approximately 1.5:1 and approximately 4:1.

8. The occlusion device of claim 1, wherein at least one of the parallelogram-shaped openings has an upward attitude and at least one of the parallelogram-shaped openings has a downward attitude.

9. The occlusion device of claim 8, wherein the parallelogram-shaped openings are arranged in longitudinally extending rows, and wherein the parallelogram-shaped openings of adjacent rows have opposite attitudes.

10. The occlusion device of claim 8, wherein the upward attitude and the downward attitude each are at an angle as manufactured that is less than said opening angle of between about 5 and about 30 degrees.

11. The occlusion device of claim 1, wherein the longer edge of the opening is adjacent to part of at least two other openings.

12. An occlusion device for occluding at least a portion of a body vessel in a human subject, comprising:
   a generally tubular support member radially expandable from a compressed condition to an expanded condition for occlusion action within a body vessel, wherein the support member has a porosity at least in the expanded condition;
   a generally tubular screen member received on at least a portion of the support member and radially and circumferentially expandable from a radially and circumferentially compressed condition to a radially and circumferentially expanded condition with the support member, said screen member having a plurality of parallelogram-shaped openings in the compressed condition, and wherein the screen member is a thin-film mesh from which the parallelogram-shaped openings had been cut to be circumferentially adjacent to each other and are in a common cylindrical plane, and the screen member has a porosity in the expanded condition less than the porosity of the support member in the expanded condition;
   each said opening is defined by a pair of upwardly inclined parallel edges at an upward attitude and directly intersecting a pair of downwardly inclined parallel edges at a downward attitude, adjacent edges defining an as-manufactured opening angle that is between about 5 and about 30 degrees, wherein upwardly inclined and downwardly inclined designate a general relationship with respect to the longitudinal axis of the screen member, and wherein one of the pairs of parallel edges is at least twice as long as the other one of the pairs of parallel edges;
   said upward attitude and downward attitude each are at an angle less than said opening angle of between about 5 degrees and about 30 degrees;
   said screen member has an opening-to-material ratio falling within the range of approximately 1.5:1 and approximately 4:1; and
   respective lowermost ends of adjacent upwardly inclined and downwardly inclined parallel edges of the opening directly engage each other to directly define vertex that joins said opening with an adjacent opening offset therefrom in that the vertex is at a location spaced away from and between the ends of a said longer edge of the adjacent opening, whereby openings of adjacent rows of openings are axially offset from each other within the common cylindrical plane such that the openings from adjacent rows are not in circumferential alignment with each other.

13. The occlusion device of claim 12, wherein an edge of the screen member has a generally sinusoidal configuration.

14. An occlusion device for occluding at least a portion of a body vessel in a human subject, comprising:
   a generally tubular support member radially expandable from a compressed condition to an expanded condition for occlusion action within a body vessel, wherein the support member has a porosity in at least the expanded condition;
   a generally tubular screen member attached to the support member and radially and circumferentially expandable from a radially and circumferentially compressed condition to a radially and circumferentially expanded condition with the support member, further comprising a plurality of parallelogram-shaped openings in the compressed condition, and wherein the screen member is a thin-film mesh from which the parallelogram-shaped openings had been cut to be circumferentially adjacent to each other and are in a common cylindrical plane, and the screen member has a porosity in the expanded condition less than the porosity of the support member in the expanded condition, the porosity of the screen member being at least about 60%;
   said openings are defined by a pair of upwardly inclined parallel edges directly intersecting a pair of downwardly inclined parallel edges, wherein upwardly inclined and downwardly inclined designate a general relationship with respect to the longitudinal axis of the screen member, and wherein one of the pairs of parallel edges is at least about 1.5 times longer than the other one of the pairs of parallel edges and adjacent intersecting edges define an opening angle;
   said opening angle as manufactured is between about 5 degrees and about 30 degrees;
   the parallelogram-shaped openings of the screen member are arranged in rows, and the parallelogram-shaped openings of adjacent rows of the screen member have opposite attitudes; and
   respective lowermost ends of adjacent upwardly inclined and downwardly inclined parallel edges of the opening directly engage each other to directly define vertex that joins said opening with an adjacent opening offset therefrom in that the vertex is at a location spaced away from and between the ends of a said longer edge of the adjacent opening, whereby openings of adjacent rows of openings are axially offset from each other within the common cylindrical plane such that the openings from adjacent rows are not in circumferential alignment with each other.

15. The occlusion device of claim 14, wherein an edge of the outer screen member has a generally sinusoidal configuration.

16. The occlusion device of claim 14, wherein said screen members each have an opening-to-material ratio falling within the range of approximately 1.5:1 and approximately 4:1.

17. The occlusion device of claim 14, wherein at least one of the parallelogram-shaped openings of the screen member has an upward attitude and at least one of the parallelogram-shaped openings of the screen member has a downward attitude.

\* \* \* \* \*